(12) United States Patent
Thompson et al.

(10) Patent No.: US 9,950,187 B2
(45) Date of Patent: *Apr. 24, 2018

(54) SYSTEM AND METHOD FOR THERAPY AND DIAGNOSIS COMPRISING OPTICAL COMPONENTS FOR DISTRIBUTION OF RADIATION

(71) Applicant: SPECTRACURE AB, Veberod (SE)

(72) Inventors: Marcelo Soto Thompson, Malmö (SE); Stefan Andersson Engels, Höör (SE); Sune Svanberg, Lund (SE)

(73) Assignee: SPECTRACURE AB, Veberod Country (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/283,105

(22) Filed: Sep. 30, 2016

(65) Prior Publication Data

US 2017/0021189 A1 Jan. 26, 2017

Related U.S. Application Data

(63) Continuation of application No. 10/556,522, filed as application No. PCT/SE2004/000756 on May 14, 2004, now Pat. No. 9,486,640.

(30) Foreign Application Priority Data

May 14, 2003 (SE) ...................................... 0301410

(51) Int. Cl.
*A61B 6/00* (2006.01)
*A61N 5/06* (2006.01)
(Continued)

(52) U.S. Cl.
CPC .......... *A61N 5/0601* (2013.01); *A61B 5/0071* (2013.01); *A61B 5/0084* (2013.01);
(Continued)

(58) Field of Classification Search
CPC ........................... A61B 5/0059; A61B 5/0075
See application file for complete search history.

(56) References Cited

U.S. PATENT DOCUMENTS

| 4,155,816 A | 5/1979 | Marencak |
|---|---|---|
| 4,491,384 A | 1/1985 | Yamashita et al. |

(Continued)

FOREIGN PATENT DOCUMENTS

| EP | 0195375 A2 | 9/1986 |
|---|---|---|
| EP | 0280397 | 8/1988 |

(Continued)

OTHER PUBLICATIONS

EPO Communication pursuant to Article 94(3) EPC dated Mar. 1, 2012 in 5 pages.

(Continued)

*Primary Examiner* — Hien Nguyen
(74) *Attorney, Agent, or Firm* — Knobbe, Martens, Olson & Bear, LLP (57) ABSTRACT

A system and method for interactive therapy and diagnosis of a human or animal comprising at least one first radiation source for emission of a diagnostic radiation, at least one second radiation source for emission of a therapeutic radiation, and at least one radiation conductor adapted to conduct radiation to a tumor site at or in said human or animal. A non-mechanical operation mode selector directs the therapeutic radiation and/or the diagnostic radiation to the tumor site through the radiation conductors. The operation mode selector means is preferably a non-mechanical optical switch and/or an optical combiner. The system may be used for interactive interstitial photodynamic tumor therapy.

14 Claims, 4 Drawing Sheets

(51) Int. Cl.
*A61B 5/00* (2006.01)
*A61B 17/00* (2006.01)
*A61B 18/20* (2006.01)
*A61N 5/067* (2006.01)

(52) U.S. Cl.
CPC .... *A61N 5/062* (2013.01); *A61B 2017/00057* (2013.01); *A61B 2018/208* (2013.01); *A61N 2005/063* (2013.01); *A61N 2005/067* (2013.01); *A61N 2005/0612* (2013.01); *A61N 2005/0629* (2013.01); *A61N 2005/0659* (2013.01); *A61N 2005/0661* (2013.01); *A61N 2005/0662* (2013.01); *A61N 2005/0663* (2013.01)

(56) References Cited

U.S. PATENT DOCUMENTS

| | | | |
|---|---|---|---|
| 4,768,513 A | | 9/1988 | Suzuki |
| 4,981,138 A | | 1/1991 | Deckelbaum et al. |
| 5,128,797 A | | 7/1992 | Sachse et al. |
| 5,321,774 A | | 6/1994 | Barnard et al. |
| 6,090,103 A | * | 7/2000 | Hakky ........... A61B 17/320758 604/20 |
| 6,138,046 A | | 10/2000 | Dalton |
| 6,975,898 B2 | | 12/2005 | Seibel |
| 2002/0076142 A1 | | 6/2002 | Song |
| 2002/0171905 A1 | | 11/2002 | Liu et al. |
| 2002/0186921 A1 | | 12/2002 | Schumacher et al. |
| 2002/0193849 A1 | * | 12/2002 | Fenn ........................ A61N 5/02 607/89 |
| 2003/0004557 A1 | * | 1/2003 | Neuberger ............. A61B 18/22 607/89 |
| 2007/0060982 A1 | | 3/2007 | Johansson et al. |
| 2007/0135873 A1 | | 6/2007 | Johansson et al. |

FOREIGN PATENT DOCUMENTS

| | | |
|---|---|---|
| GB | 2126717 A | 3/1984 |
| JP | 60-14840 | 1/1985 |
| JP | 3-126449 | 5/1991 |
| JP | 4-7850 | 1/1992 |
| JP | 8-33646 | 2/1996 |
| SE | 503 408 C2 | 6/1996 |
| WO | WO 0197902 | 12/2001 |
| WO | WO 02074339 | 9/2002 |
| WO | WO 2004/112902 | 12/2004 |

OTHER PUBLICATIONS

Japanese Office Action, dated Dec. 7, 2009, Application No. 2006-532192.

Thomas Johansson, et al, Feasibility study of a system for combined light dosimetry and interstitial photodynamic treatment of massive tumors, Applied Optics, vol. 41, No. 7.

International Search Report for International Patent Application No. PCT/SE2004/000756 dated Sep. 7, 2004 in 4 pages.

\* cited by examiner

SYSTEM AND METHOD FOR THERAPY AND DIAGNOSIS COMPRISING OPTICAL COMPONENTS FOR DISTRIBUTION OF RADIATION

CROSS-REFERENCE TO RELATED APPLICATION(S)

The present Application is a continuation U.S. patent application Ser. No. 10/556,522, filed Oct. 2, 2006, titled "System and Method For Therapy and Diagnosis Comprising Optical Components for Distribution of Radiation," which claims the benefit and priority of National Stage Application PCT/SE04/00756, filed May 14, 2004, which claims the benefit and priority of Swedish Application No. 0301410-7, filed May 14, 2003, the contents of each of which are incorporated in this disclosure by reference in their entirety.

FIELD OF THE INVENTION

The invention relates generally to a system and a method for therapy and diagnosis in a subject. More particularly, the system and method relate to a system and method for tumour therapy and diagnosis in a human or animal subject. Even more particularly, the invention relates to a system and method for photodynamic therapy (PDT) and/or photothermal therapy (PTT) and/or photodynamic diagnosis (PDD) of a site on and/or in a human or animal body, wherein electromagnetic non-ionising radiation is conducted to the site for reaction with the radiation, wherein the system comprises an operation mode selector for distribution of radiation from at least one source of radiation to a reaction site, and/or from the reaction site to at least one radiation sensor, respectively, and wherein the reaction site generally is a tumour site with a tumour, such as a malignant tumour.

BACKGROUND OF THE INVENTION

Within the field of medical therapy of tumour diseases, a plurality of treatment modalities has been developed for the treatment of malignant tumour diseases: operation, cytostatic treatment, treatment with ionising radiation (gamma or particle radiation), isotope therapy and brachytherapy employing radioactive needles are examples of common treatment modalities. In spite of great progress within therapy, the tumour diseases continue to account for much human suffering, and are responsible for a high percentage of deaths in western countries. A relatively new treatment modality, photodynamic therapy, commonly abbreviated PDT, provides an interesting complement or alternative in the treatment field. A tumour-seeking agent, normally referred to as a precursor or sensitizer, is administered to the body e.g. intravenously, orally or topically. It generally accumulates in malignant tumours to a higher extent than in the surrounding healthy tissue. The tumour area is then irradiated with non-thermal red light, normally from a laser, leading to excitation of the sensitizer to a more energetic state. Through energy transfer from the activated sensitizer to the oxygen molecules of the tissue, the oxygen is transferred from its normal triplet state to the excited singlet state. Singlet oxygen is known to be particularly toxic to tissue; cells are eradicated and the tissue goes in necrosis. Because of the localisation of the sensitizer to tumour cells a unique selectivity is obtained, where surrounding healthy tissue is spared. The clinical experiences, using in particular haematoporphyrin derivative (HPD) and delta aminolevulinic acid (ALA) have shown good results.

Sensitizers may also exhibit a further useful property; when the substance is excited with visible or ultraviolet radiation it will yield a characteristic fluorescence signal, shifted towards longer wavelengths. This signal clearly appears in contrast to the endogenous fluorescence of the tissue, which is also called autofluorescence, and is used to localise tumours and for quantifying the size of the uptake of the sensitizer in the tissue.

The limited penetration in the tissue of the activating red radiation is a big drawback of PDT. The result is that only tumours less than about 5 mm thickness can be treated by surface irradiation. In order to treat thicker and/or deep-lying tumours, interstitial PDT (IPDT) can be utilised. Here, light-conducting optical fibres are brought into the tumour using, e.g. a syringe needle, in the lumen of which a fibre has been placed.

In order to achieve an efficient treatment, several fibres have been used to ascertain that all tumour cells are subjected to a sufficient dose of light so that the toxic singlet state is obtained. It has been shown to be achievable to perform dose calculations of the absorptive and scattering properties of the tissue. E.g., in the Swedish patent SE 503 408 an IPDT system is described, where six fibres are used for treatment as well as for measurement of the light flux which reaches a given fibre in the penetration through the tissue from the other fibres. In this way an improved calculation of the correct light dose can be achieved for all parts of the tumour.

According to the disclosure of SE 503 408, the light from a single laser is divided into six different parts using a beamsplitter system comprising a large number of bulky mechanical and optical components. The light is then focused into each of the six individual treatment fibres. One fibre is used as a transmitter while the other fibres are used as receivers of radiation penetrating the tissue. For light measurement light detectors are mechanically swung into the beam path which thus is blocked, and the weak light, which originates from the fibres that collected the light which is administered to the tissue, is measured.

However, such open beam paths result in a strongly lossy beamsplitting and the resulting losses of light drastically impair the light distribution as well as the light measurement. Furthermore, such a system must often be adjusted optically, which is also an important drawback in connection with clinical treatments. The system is also large and heavy and difficult to integrate into a user-friendly apparatus.

EP-A2-0280397 discloses a sterilizable endoscope of small diameter having a central coherent fibre bundle for carrying an image to a viewing means. The fibre bundle is surrounded by light fibres. The proximate end of the endoscope is provided with a coupling means for aligning the optical fibre bundle with the optical system of the viewing means and for providing an interface with light transmitting means to transmit light from a light source along the light fibres to a body cavity to be inspected. The device can be used for detection of cancer cells and treatment thereof by phototherapy. A dye is attached to the tissue being examined and subsequently exposed to an exciting laser light frequency. Cancer cells will emit fluorescent light at a characteristic fluorescence frequency. The fluorescence light is detected and displayed on the video monitor and light with the same frequency as this fluorescent light is then transmitted through the light fibres to the cell for phototherapy treatment. However, only the use of a single wavelength light source is disclosed, it is thus not possible to have multiple diagnostics performed without manually exchanging the light source. Moreover, it is not possible to switch between different constellations of the light fibres, i.e. all fibres always have the same function (light in or light out). The coupling means mentioned in EP-A2-0280397 is only used to adjust the path of light through a two-part endoscope when it is assembled prior to use. In addition, different fibres are used for directing therapeutic light to a cancer location and to direct diagnostic light back through the endoscope. No distribution is performed between different operating modes. This solution offers for instance neither interactive treatment nor tomographic mapping of tumours. WO-A1-02074339 discloses a device and method for photodynamic diagnosis of tumour tissue by using fluorescent cobalamins. These fluorescent cobalamins are used as diagnostic and prognostic markers (a) to distinguish cancer cells and tissues from healthy cells and tissues, and (b) to determine if an individual responds positively to chemotherapy using cobalamin-therapeutic bioconjugates. An apparatus is disclosed that includes a camera coupled to the proximal end of a surgical telescopic device. The surgical telescopic device is used for illuminating tissue with non-white light and detecting the emitted fluorescence for diagnostic purposes. The use of a dual light sources including a red (non-white) and a white light source is disclosed. The white light source is used for conventional illumination of the tissue. A switch is mentioned for switching between the alternative light sources. The switch might be voice-actuated, mechanically-operated (foot pedal), optically-operated, or electronically-operated. The switch is not described in more detail, except that a mirror or prism under mechanical or electromechanical control can be used to switch between the two light sources. Alternatively, a light source with two physically separated outputs is disclosed. In this case the light input to the surgical telescopic device has to be moved between the two outputs in order to switch illumination source for the tissue. The device is not suitable for therapy. Therapy has to be performed conventionally by a surgeon removing the cancerous tissue detected by means of fluorescence. Therefore, this device is not suited for interactive diagnosis and therapy. Furthermore, there is no indication for a switch suitable for switching between different modes of diagnosis or therapy. Furthermore, the disclosed device offers only substantially superficial diagnosis or treatment, interstitial tissue cannot be diagnosed or treated. The device is also limited to existing body cavities and has the drawback that endoscopic probes are bulky and large compared to single optical fibres.

EP-A2-0195375 discloses a catheter for laser angiosurgery. The device is used for detecting atherosclerotic plaque deposits by means of detecting fluorescent light as a reaction on excitation light sent through the catheter comprising optical fibres for this purpose. The same fibre may be used for sending excitation light to the plaque and for receiving fluorescent light from the plaque. When plaque is detected, it may be removed by sending high energy light through selected fibres in the catheter. However, this system is not suited for diagnosis or treatment of tumours. Fibres to be illuminated are selected by purely mechanical arrangements either moving the light source or the fibres in order to align the two towards each other. This device is also bulky compared to single fibres, similar to the above mentioned endoscope, bound to existing body cavities and works substantially superficial. Furthermore it is not selective, i.e. all tissue aimed at is destroyed, independently if it is noxious or healthy.

Thus, there is a need for a new compact device allowing distributing of radiation in a system for PDD, PDT and PTT for implementing a smart way of performing interactive interstitial treatment. One solution would be to use smart mechanical constructions for switching between different modes avoiding e.g. the lossy beamsplitters and allowing e.g. automatic calibration.

Such a mechanical solution to the above mentioned problems has been proposed in PCT/SE02/02050, wherein a distributor for radiation having two discs rotating relative to each other is described. The radiation distributor couples optical fibres between different modes by rotational movement of fibres in these discs relative each other. For switching between several light sources to one fibre going to the patient, an assembly with a total of four discs is described.

However, although these mechanical constructions are improvements to the above described known IPDT system and although the above described problems are solved, these mechanical solutions have other limitations, related to e.g. mechanical inertia limiting the switching time between the different modes of a therapy and diagnosis system such as an interactive interstitial treatment system.

Thus, there is a need for a new compact device allowing distributing of radiation in a system for therapy and diagnosis in a human or animal, wherein the therapy and diagnosis comprises PDT, PTT, and PDD.

Further problems to be solved by the invention are to provide an alternative solution eliminating the service of components e.g. due to wear of components, thus improving reliability of a device for therapy and diagnosis comprising PDT, PTT, and PDD. Also, the rotation of the fibres should be avoided, which further reduces the necessary size of the device and increases reliability. Furthermore, another problem solved by the invention is that sounds or noises that are generated in operation of known devices when switching between different operation modes are substantially reduced or eliminated.

SUMMARY OF THE INVENTION

The present invention overcomes the above identified deficiencies in the art and solves at least the above identified problems by providing a system and a method according to the appended patent claims, wherein a very practical and efficient implementation of interactive IPDT is achieved in that different optical measurements for diagnostics and dosimetry can be performed in an integrated and simple way by means of a system requiring minimal space. An important application of the invention is interactive, interstitial photodynamic therapy, and/or interactive photothermal tumour therapy.

The term "radiation" used hereinafter in this specification refers to radiation suitable for the field of the invention, i.e. for photodynamic therapy (PDT) and/or photothermal therapy (PTT) and/or photodynamic diagnosis (PDD). More specifically this radiation is "optical" radiation, i.e. non-ionising electromagnetical radiation within the wavelength-range of infrared (IR), visible or ultraviolet light. This also concerns radiation sources, radiation conductors, radiation sensors, radiation switches etc. within the scope of the embodiments and claims defining the invention, i.e. these sources, conductors or sensors for "radiation" are adapted to generate, conduct, measure, etc. the above-mentioned non-ionising radiation.

According to one aspect of the invention, a system for therapy and/or diagnosis of a human or animal comprises at least one first radiation source for emission of a diagnostic radiation and at least one second radiation source for emission of a therapeutic radiation, and at least one first radiation conductor adapted to conduct radiation to a site of the human or animal. The system comprises an operation mode selector means for optically directing either said therapeutic radiation or said diagnostic radiation to said site through said at least one first radiation conductor.

According to an embodiment of the invention, the system for therapy and/or diagnosis of a human or animal is a system and method for interactive interstitial photodynamic tumour therapy and/or photothermal tumour therapy and/or tumour diagnosis.

The use of non-mechanical switching elements based on optical principles offers several advantages over mechanical arrangements. Among others, these advantages comprise: high switching speed between different system operation modes (diagnosis, photodynamic therapy, thermal therapy); compactness and stability of the system; excellent optical parameters; long life of the system due to no mechanical wear of the components and due to many more switching cycles during a life-cycle of the elements of the system; and no switching noise, thus offering increased patient comfort.

BRIEF DESCRIPTION OF THE DRAWINGS

In order to explain the invention more detailed, a number of embodiments of the invention will be described below with reference to the appended drawings, wherein.

DESCRIPTION OF EMBODIMENTS

Different embodiments of the system according to the invention are now described with reference to the drawings. In order to simplify the description of the embodiments, reference numerals for similar elements shown in the drawings are not repeated throughout all the figures.

Figure 1:
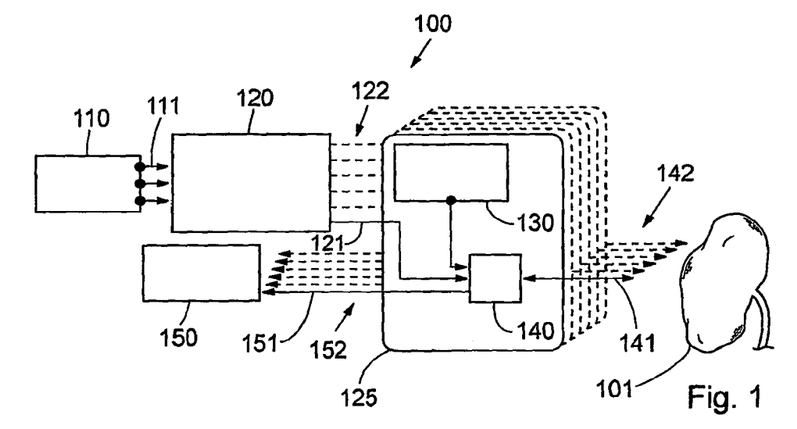
FIG. 1 is a schematic view illustrating an embodiment of the invention for interactive IPDT.

A general description of a system 100 according to a first embodiment of the invention is given with reference to FIG. 1. Accordingly, a system 100 for interactive IPDT comprises at least one diagnostic radiation source 110. The diagnostic radiation source 110 generates a diagnostic radiation. The optical radiation from at least one diagnostic optical radiation source 110 enters a diagnostic optical radiation coupling module 120. The optical radiation is preferably transmitted by means of optical radiation conductors 111. In general, the radiation conductors, described in this description of embodiments, are light guides such as optical fibres. The diagnostic radiation coupling module 120 distributes the radiation further through one or more radiation conductors 122 to at least one corresponding operation mode selection module 140. The coupling of the diagnostic radiation to the radiation conductors 122 is accomplished by means of the diagnostic radiation coupling module 120, which e.g. comprises a non-mechanical optical switch or alternatively an optical combiner in series with a non-mechanical optical switch or alternatively with an optical combiner. This will be explained in more detail below.

The diagnostic radiation is further conducted to one of the operation mode selection modules 140, as shown in FIG. 1. The purpose of each operation mode selection module 140 is to guide diagnostic radiation from one of the diagnostic radiation sources 110 or therapeutic radiation from therapeutic radiation sources 130 through one of radiation conductors 142 to a treatment site 101 in a patient. All these radiation conductors 142 can transmit radiation to the reaction site 101 and receive radiation from said site. Thus, several measurements can be recorded and read out simultaneously. Each of the fibres 142 is proximally coupled to a separate operation mode selection module 140, e.g. fibre 141 is coupled to the operation mode selection module 140 illustrated as the first operation mode selection module of a plurality 125 of operation mode selection modules 140/ therapeutic radiation sources 130 in FIG. 1. The distal end of fibres 142 are appropriately positioned in different locations at the treatment site in order to enable an effective diagnosis or treatment of the patient. Moreover, the operation mode selection modules 140 couple radiation, which is transmitted from the distal end of fibres 142 back towards the operation mode selection module 140, further towards at least one radiation detector 150. Alternatively a plurality of radiation detectors is used, either with different sensitivities or e.g. one detector for each operation mode selection module. The radiation coming from the treatment site 101 is transmitted to the radiation detectors 150 by means of radiation conductors 152, wherein a radiation conductor 151 is illustrated going from the topmost illustrated operation mode selection module 140 to radiation detector 150. The operation mode selection module 140 may comprise e.g. a non-mechanical optical switch or an optical combiner. An embodiment of an operation mode selection module 140 based on an optical combiner is described in more detail below with reference to FIG. 4.

Figure 2:
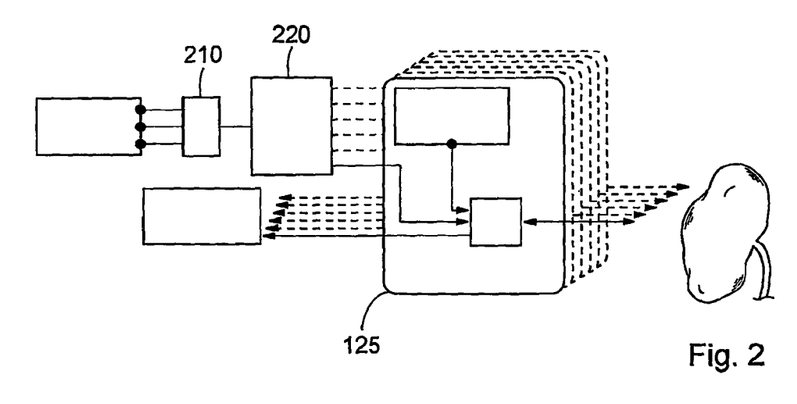
FIG. 2 is a schematic view illustrating another embodiment of the invention.
Figure 5:
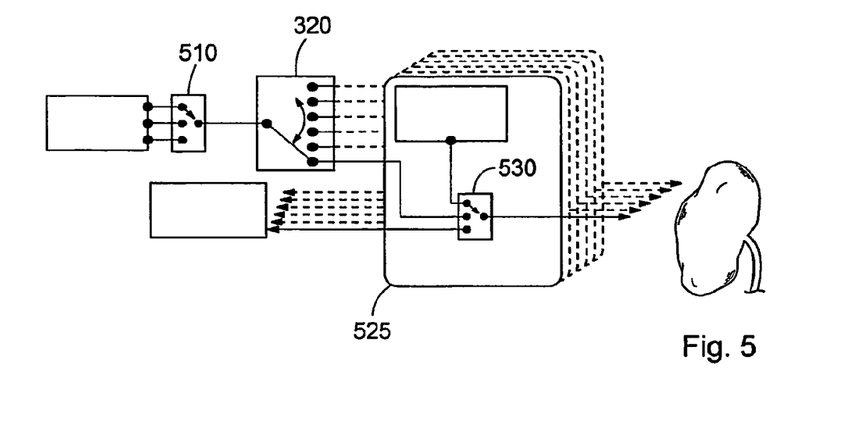
FIG. 5 is a schematic view illustrating another embodiment of the invention comprising non-mechanical optical switches.

FIG. 2 illustrates another embodiment of an interactive interstitial treatment system, wherein the diagnostic radiation coupling module 120 is subdivided into two radiation distributor components 210 and 220. Radiation distributor 210 is as illustrated, a (N×1) radiation distributor, i.e. a radiation distributor having N radiation inputs and one radiation output. In the illustrated example, the radiation distributor 210 is a 3×1 radiation distributor, which single output is coupled to a (1×n) radiation distributor 220, wherein n is the number of operation mode selection modules 125 as well as the number of radiation conductors 142 going to/from the treatment site 101. Radiation distributors 210, 220 may comprise, similar to operation mode selection module 140, e.g. a non-mechanical optical switch or an optical combiner. Exemplary radiation distributors 210, 220 are described in more detail below with reference to FIGS. 3 and 5 illustrating different combinations of non-mechanical optical switches and/or combiners for radiation distributors 210, 220 and selection module 140 have different advantages concerning e.g. performance of the system.

Figure 3:
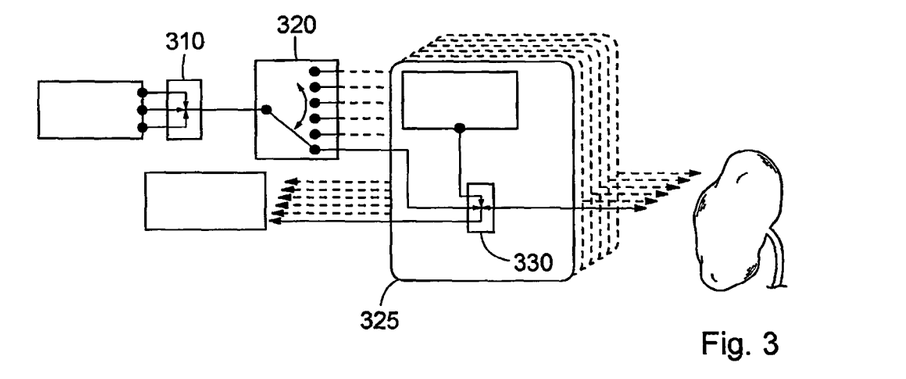
FIG. 3 is a schematic view over a further embodiment of the invention comprising optical combiners and a non-mechanical optical switch.

In FIG. 3, a system is shown comprising an optical 3×1 combiner 310 and an non-mechanical optical 1×6 switch 320 as well as an optical combiner 330 as a operation mode selector in six modules 325. For interstitial treatment six therapeutic radiation sources 130, preferably laser light modules, are coupled to the six optical combiners 330. Each optical combiner 330 works in such a manner that the therapeutic radiation in therapy operation mode is coupled through the corresponding radiation conductor 142 to the treatment site 101. For switching to the diagnostic operation mode, the therapeutic radiation source is switched off and subsequently one of the three diagnostic radiation sources 110 is activated. Thus, diagnostic radiation is conducted to combiner 310, where the radiation from the active diagnostic radiation source is coupled to the output of the combiner leading to the non-mechanical optical switch 320. The non-mechanical optical switch 320 couples the input radiation to an output radiation conductor 122 leading to the corresponding optical combiner 330 comprised in one of modules 325. From combiner 330, the diagnostic radiation is sent to the treatment site via a radiation conductor 142 connected to combiner 330, as shown in FIG. 3. Thus the diagnostic radiation is spread in the treatment site and partly to the remaining five radiation conductors 142 and partly reflected back. The diagnostic radiation from the patient is via combiner 330 sent to radiation detector 150. Thus five (=(n−1)) measurement values are obtained. Subsequently the non-mechanical optical switch 320 switches the incoming diagnostic radiation from the radiation source 110 to the next combiner 330 comprised in the next module 325. Thus five further measurement values are obtained. This measurement procedure is repeated until all six modules 325 have been activated, resulting in six times five (=30) measurement values. These thirty measurement values obtained may be used as input data for a tomographic modelling of the optical dose build up in the different parts of the tumour during the course of the treatment. This measurement procedure may be repeated with the remaining diagnostic radiation sources, yielding three times thirty (N*(n−1)) or ninety tomographic measurement values. Also the diagnostic radiation reflected at site 101 from the illuminating radiation connector may be used for diagnostic purposes.

The combiner 310 may be a fibre combiner commercially available from, e.g., Polymicro Technologies or Sedi Fibres Optiques.

Figure 4:
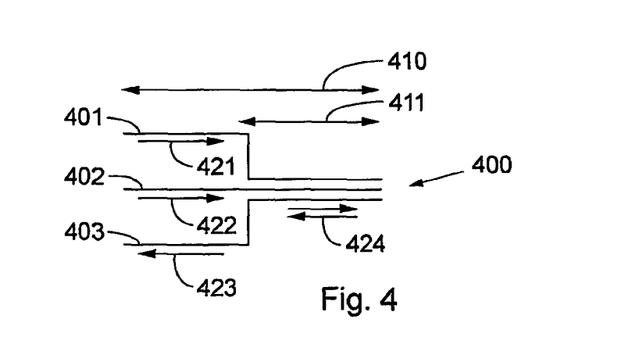
FIG. 4 is a schematic view illustrating the principle of an optical combiner used in an embodiment of the invention.

As a basis for the non-mechanical optical switch 320 one may use a commercially available optical fibre switch from Piezosystem Jena Inc or Agiltron Inc. The working principle of the combiner 330 is illustrated in FIG. 4. The combiner 330 may also be based upon a commercially available fibre combiner from Polymicro Technologies. The combiner has three input fibres 401-403, wherein radiation is transmitted along these fibres in the directions as indicated by arrows 421-423. The fibres 401-403 are drawn together to a single fibre along a length as indicated by arrow 411 or fused at the junction of 401, 402, 403, and 424. The whole combiner has a length as indicated by arrow 410. Thus optical radiation is transmitted via the fibres 401 and 402 to the single fibre at 400 and radiation from the single fibre at 400 is transmitted in the opposite direction mainly to fibre 403. In the embodiment according to FIG. 3, fibre 401 is connected to the therapeutic radiation source, fibre 402 is connected to the diagnostic radiation source and fibre 403 is connected to the radiation detector. The combiner 330 can be made to transmit the main part of the diagnostic radiation emerging from the tissue site 101 via fibre 400 to fibre 403, assuring an efficient use of the occasionally faint diagnostic radiation. The combiner does not transmit radiation directly from fibres 401,402 to fibre 403.

FIG. 5 is a schematic diagram illustrating a further embodiment of the present invention, wherein a non-mechanical optical switch 510 switches between different diagnostic radiation sources 110. A further non-mechanical optical switch 530 works as an operation mode selector, wherein either the therapeutic radiation source is coupled to the treatment site, the diagnostic radiation source is coupled to the treatment site, or the treatment site is coupled to the radiation detector. The non-mechanical optical switch 320 works similar as described above. This embodiment has the advantage that the time for switching from one diagnostic radiation source to another is not determined by the diagnostic radiation sources. Compared to an optical combiner, the non-mechanical optical switch 510 determines the time needed for switching between different radiation sources. This is in general more reproducible than turning off a light source at one input of a combiner and turning on another light source at another input of a combiner, wherein both light sources are coupled to the same output of the combiner. Furthermore a non-mechanical optical switch generally exhibits lower radiation losses than an optical combiner, which means that less powerful diagnostic radiation sources may be used than with optical combiner 310. However, a non-mechanical optical switch has to be actively controlled, whereas an optical combiner is a passive component. Moreover, the non-mechanical optical switch 530 prevents reflected diagnostic radiation from entering the radiation detector 150 via a combiner, e.g. combiner 330. This unintended diagnostic radiation going to the detector may lead to "blooming" (saturation) of the detector 150. Instead of using a plurality of detectors 150 in order to avoid this phenomena, a single detector may be sufficient, which limits costs of the system according to the present embodiment.

Figure 6:
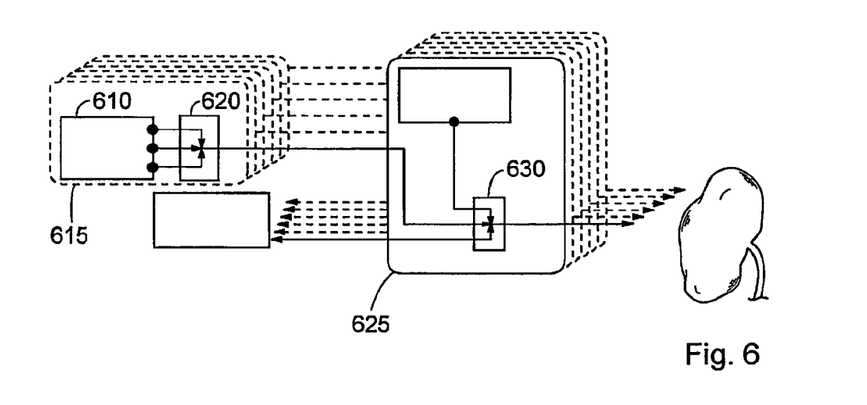
FIG. 6 is a schematic view showing yet a further embodiment of the invention comprising modules with multiple diagnostic radiation sources.

FIG. 6 is a schematic diagram illustrating yet a further embodiment of the present invention. An optical combiner 630 is used similarly to the optical combiner 330. A plurality of diagnostic radiation sources 610, each having a corresponding combiner 620 in a plurality of diagnostic radiation source modules 615, is comprised in this embodiment instead of an optical switch distributing the diagnostic radiation to a plurality of operation mode selection modules 140. Thus the cost for an optical switch, e.g. switch 320, is avoided. Furthermore the diagnostic radiation sources 610 may be modulated, so that the diagnostic radiation may be detected simultaneously by means of e.g. a lock-in technique or by multiplexing the signals.

Figure 7:
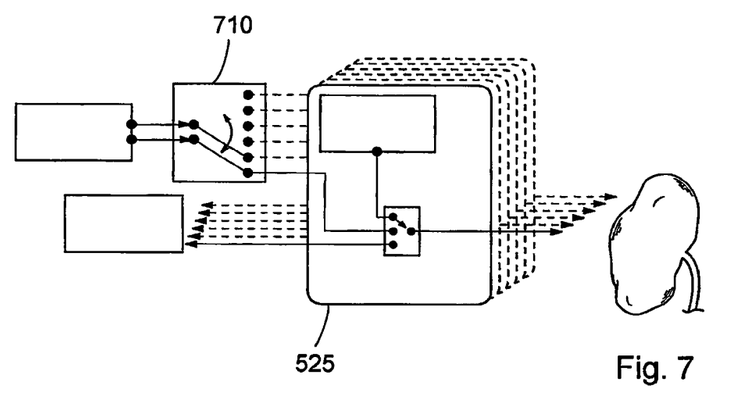
FIG. 7 is a schematic view showing yet a further embodiment of the invention comprising a 2×N non-mechanical optical switch.

FIG. 7 is a schematic diagram illustrating yet another embodiment of the present invention. The embodiment comprises an optical 2×n switch 710 coupling two diagnostic input radiation sources to n outputs of the switch 710. The switch 710 has two inputs, which may arbitrarily be directed to the different outputs. Such components are commercially available from e.g. Pyramid Optics. The operation mode selector/therapeutic radiation source module is an operation mode selector module 525 as described with reference to FIG. 5, but might also be replaced by a combiner module 625. In this way a more compact solution is achieved, as there is one component less in the system, e.g. combiner 310 or switch 510. An optical switch has also lower losses than a combiner, as already mentioned above.

The radiation conductors may be coupled to or connected to the different elements of the system according to the invention by any suitable method or means, including fibre optic connectors of different types, such as SMA, ST or FC connectors. Alternatively, the radiation conductors may be fixed in holes by appropriate methods, e.g. glueing or mechanically fastening by, e.g., spring loaded elements.

For calibration purposes of the system according to the invention, the overall performance of the system is recorded prior to the treatment by direct measurements on a calibrated tissue phantom made of, e.g., a sterile intralipid-water solution or a sterile solid phantom made of, e.g., Delrin®. The performance of the therapeutic radiation sources may either be monitored by internal and/or external power meters.

The non-mechanical optical switches described may work according to different principles. The switching and beam deflection is based on optical principles without mechanical movement of components such as prisms or mirrors. Examples of switching principles are for instance beam deflection by an acousto-optical means, or acousto magnetic means, or by an electrically controlled variation of the refractive index of a material through which the beam travels, thereby deflecting an optical beam to different output/input fibres. Examples for materials having a variable refractive index suitable for electro-optical switches are e.g. $LiNbO_3$, $LiTaO_3$, GaAs, HgS, CdS, KDP, ADP or $SiO_2$. The Agiltron™ company provides commercially available optical switches of this type, namely the CrystaLatch™ Solid-State Fiber Optic Switch family or the NanoSpeed™ Optical Switch Series. These optical switches feature fast response and ultra-high reliability exceeding 100 billion switching cycles. The Agiltron™ are an example for truly non-mechanical (zero moving parts) optical switches, which are activated by an electrical pulse inside an inorganic optical crystal to facilitate state-of-the-art switching. Switching is furthermore performed intrinsically stable against temperature fluctuation and fatigue, providing another advantage of non-mechanical switches. In addition, the Agiltron switches provide fail-safe latching capability, thereby maintaining their position indefinitely when power is removed The switches are conveniently controllable by a direct low voltage signal or digitally.

In the following section, basic principles related to the system according to the invention will be described, wherein the description is based on an exemplary system with three diagnostic radiation sources 110 and six patient radiation conductors 142, preferably optical fibres.

By a reaction or treatment site we mean in the present context a site, where photodynamically active compounds will react in a tumour when subject to therapy radiation e.g. conducted by radiation conductors being forwarded through e.g. the lumen of injection needles which are placed in the tumour. These radiation conductors 142 are then fixed in the reaction site 101. Then the radiation conductors are moved forward to arrive outside the distal end of the needle. The same radiation conductor 142 is used continuously during the treatment for integrated diagnostics and dosimetry as well as to avoid that the patient be subjected to multiple pricks.

Preferably the diagnostic radiation sources 110 are lasers and/or light emitting diodes, out of which one is of the same wavelength as the lasers 130 utilised for the laser irradiation for photodynamic tumour therapy, but could be of lower output power. Suitable filters can be arranged to be inserted into the light path of the radiation sensor 150 in order to secure that the correct dynamic range is utilised for all measurement tasks and in order to prevent the above mentioned "blooming" of the radiation detector.

Certain of the diagnostic radiation sources 110 are utilised in order to study how radiation (light, as defined above) of the corresponding wavelength is penetrating through the tissue of the tumour at the treatment site 101. When radiation from a radiation source is transmitted through the particular radiation conductor via the above described arrangements into the tissue, one of the radiation conductors 142, functions as a transmitter into the tumour, and the other five radiation conductors 142 in the tumour will act as receivers and collect the diffuse flux of radiation reaching them. The radiation collected is again conducted to the radiation sensor 150, as described above, and five different radiation intensities can be recorded on the detector array.

As an alternative to a specific wavelength, radiation from an optically broad light source such, as a white light source, and/or broadband light emitting diodes and/or line light sources can be coupled into the particular active radiation conductor 142. On passage through the tissue to the receiving radiation conductor 142 in the patient, the well-defined spectral distribution of the radiation source will be modified by the tissue absorption. Then, oxygenated blood yields a different signature than non-oxygenated blood, allowing a tomographic determination of the oxygen distribution utilising the thirty different spectral distributions which are read out, five spectra at a time in the six possible different constellations. Such a determination of the oxygenation in the tumour is important, since the PDT process requires access to oxygen in the tissue.

Finally, in the case of 140 being a combiner a radiation source either for visible or ultraviolet light, e.g. a laser, can be coupled to the particular active radiation conductor 142. Then fluorescence is induced in the tissue, and a sensitizer administered to the tissue displays a characteristic fluorescence distribution shifted towards longer wavelengths. The strength of the corresponding signal allows an approximate quantification of the level of the sensitizer in the tissue.

Since the short wavelength radiation has a very low penetration into the tissue, the induced fluorescence from such a source will be a local measurement at the distal tip of the radiation conductor. For this task a filter may be inserted in front of detector 150 to reduce the reflected radiation at site 101 since the reflected radiation will be many magnitudes larger than the fluorescent radiation. A suitable self-contained equipment for doing this is described in Rev. Sci. Instr. 71, 510004 (2000).

By switching the diagnostic radiation source 110 sequentially through the different modules 125, the fluorescence that is a specific function of the concentration of the sensitizer, is measured sequentially at the tips of the six radiation conductors. Since the sensitizer is bleached by the strong red treatment light, being particularly strong just around the tip of the radiation conductor 142 conducting radiation to the patient, it is essential to make this measurement before the start of the treatment.

If the tips of the radiation conductors 142 in addition are treated with a material, the fluorescence properties of which are temperature dependent, sharp fluorescence lines are obtained upon excitation, and the intensity of these lines and their relative strength depend on the temperature at the tip of the radiation conductor 142 being employed for treatment. Examples of such materials are salts of the transition metals or the rare earth metals. Thus also the temperature can be measured at the six positions of the six radiation conductors, one at a time or simultaneously. The measured temperatures can be utilised to find out if blood coagulation with an associated light attenuation has occurred at the tip of the radiation conductor 142 and for studies regarding the utilisation of possible synergy effects between PDT and thermal interaction. Since the lines obtained are sharp, they can easily be extracted from the more broad-banded endogenous fluorescence distribution from the tissue.

The sensitizer level can for certain substances be measured in an alternative way. Then the red light used for the light propagation studies is used to induce red or near-infrared fluorescence. This fluorescence penetrates through the tissue to the tips of the receiving radiation conductors 142, and is displayed simultaneously as spectra obtained in the radiation sensor 150. A tomographic calculation of the sensitizer distribution can be performed based on in total thirty measurement values at each measurement occasion.

After diagnostic measurements and calculations have been performed, the fibres 142 optically coupled to the patient can be utilised for therapy by switching off the diagnostic radiation sources and switching on the therapeutic radiation sources 130, as well as switching optical switches, if present in the system, accordingly so that therapeutic radiation sources are coupled to the patient fibres 142. The therapeutic radiation sources are preferably laser sources with a wavelength, chosen to match the absorption band of the sensitizer. At the photodynamic tumour treatment a dye laser or a diode laser is preferably used, with a wavelength which is selected with regard to the sensitizer employed. For e.g. Photofrin® the wavelength is 630 nm, for δ-aminolevulinic acid (ALA) it is 635 nm and for phthalocyanines it is around 670 nm, several other Sensitizers exist having such characteristic wavelengths. The individual lasers are regulated during the treatment to a desirable individual output power. If desired, they may have built-in or external monitoring detectors.

The therapeutic treatment may be interrupted and new diagnostic data may be processed in an interactive method until an optimal treatment has been reached. This method may include synergy between PDT and hyperthermia, where an increased temperature is reached at increased fluxes of laser radiation. The whole process is controlled using a computer, which does not only perform all the calculations but also is utilised for regulation and control of the system.

The present invention has been described above with reference to specific embodiments. However, other embodiments than the preferred above are equally possible within the scope of the appended claims, e.g. different optical coupler elements than those described above, performing the above method by hardware or software, etc.

Furthermore, the term "comprises/comprising" when used in this specification does not exclude other elements or steps, the terms "a" and "an" do not exclude a plurality and a single processor or other units may fulfil the functions of several of the units or circuits recited in the claims.

The invention claimed is:

1. A system for interactive interstitial photodynamic or photothermal tumour therapy or tumour diagnosis of a human, said system comprising:
   at least one diagnostic light source for emission of diagnostic light within a wavelength-range of infrared, near-infrared, visible or ultraviolet light;
   at least one light detector for detection of light;
   a plurality of optical fibers; and
   a plurality of modules, wherein each module comprises:
      at least one therapeutic light source for emission of therapeutic light within a wavelength-range of infrared (IR), near-infrared, visible or ultraviolet light;
      an operation mode selector optically connected to said at least one therapeutic light source, said at least one diagnostic light source, and said at least one light detector, said operation mode selector comprising an optical combiner; and
      an optical fiber for connecting said operation mode selector interstitially with a tumour site;
   wherein said plurality of optical fibers are arranged to conduct diagnostic light from said at least one diagnostic light source to each of operation mode selectors of said plurality of modules; and
   wherein said operation mode selectors of said plurality of modules are configured to:
      in a therapeutic mode optically directing light from said at least one therapeutic light source of each of said plurality of modules, via said optical combiner, to said tumour site; and
      in a diagnostic mode optically directing said diagnostic light from said at least one diagnostic light source via at least one radiation distributor component to said tumour site through at least one of said plurality of modules, and guide light from said tumour site via said modules not conducting diagnostic light, via said optical combiner, to said at least one light detector.

2. The system according to claim 1, wherein one of said at least one radiation distributor component comprises one of: an optical combiner, a non-mechanical optical switch, two non-mechanical optical switches, and a 2×N non-mechanical optical switch.

3. The system according to claim 1, wherein each operation mode selector of said plurality of modules having a similar plurality of diagnostic light sources being coupled to each of said operation mode selector for transmission to said tumour site, wherein said operation mode selector of each of said plurality of modules is configured to couple only one diagnostic light source at a time for transmission of said diagnostic light to said tumour site.

4. The system according to claim 3, wherein one of said at least one radiation distributor component comprises one of an optical combiner and a non-mechanical optical switch.

5. The system according to claim 1, wherein ends of said plurality of optical fibers of said plurality of modules adapted to be interstitially inserted into said tumour site are treated by a material with temperature sensitive fluorescence emission.

6. The system according to claim 1, wherein one or more of said at least one diagnostic light source and said at least one therapeutic light source provides coherent light of a single fixed wave-length.

7. The system according to claim 5, wherein fluorescence is recorded through an optical fiber of a module used for transmitting diagnostic light to said tumour site.

8. The system according to claim 7, wherein:
   for interactive photodynamic therapy, said optical fibers which are treated with the material with said temperature sensitive fluorescence emission are configured to measure a temperature at said tumour site;
   a light which in use is sent to the site heats said tumour site; and
   an intensity of said light is controlled based on said measured temperature.

9. The system according to claim 1, wherein said at least one light detector comprises a plurality of light detectors and each of said plurality of light detectors is connected to a different operation mode selector of said plurality of modules.

10. The system according to claim 1, wherein said at least one light detector is a single detector connected to each of said operation mode selectors of said plurality modules.

11. A system for interactive interstitial photodynamic or photothermal tumour therapy or tumour diagnosis of a human, said system comprising:
   at least one diagnostic light source for emission of diagnostic light within a wavelength-range of infrared, near-infrared, visible or ultraviolet light;

at least one light detector for detection of light;
a plurality of optical fibers; and
a plurality of modules, wherein each module comprises:
- at least one therapeutic light source for emission of therapeutic light within a wavelength-range of infra-red (IR), near-infrared, visible or ultraviolet light;
- an operation mode selector optically connected to said at least one therapeutic light source, said at least one diagnostic light source, and said at least one light detector, said operation mode selector comprising a non-mechanical optical switch; and
- an optical fiber for connecting said operation mode selector interstitially with a tumour site;

wherein said plurality of optical fibers are arranged to conduct diagnostic light from said at least one diagnostic light source to each of operation mode selectors of said plurality of modules; and wherein said operation mode selectors of said plurality of modules are configured to:
- in a therapeutic mode optically directing light from said at least one therapeutic light source of each of said plurality of modules, via said non-mechanical optical switch, to said tumour site; and
- in a diagnostic mode optically directing said diagnostic light from said at least one diagnostic light source via at least one radiation distributor component to said tumour site through at least one of said plurality of modules, and guide light from said tumour site via said modules not conducting diagnostic light, via said non-mechanical optical switch, to said at least one light detector.

12. The system according to claim 11, wherein said non-mechanical optical switch comprises an electro-optical switch based on electrically controlled refractive index variations.

13. The system according to claim 11, wherein said non-mechanical optical switch comprises an acousto-optical switch based on sound generated Bragg deflection.

14. The system according to claim 11, wherein said non-mechanical optical switch comprises a magneto-optical switch.

* * * * *

UNITED STATES PATENT AND TRADEMARK OFFICE
CERTIFICATE OF CORRECTION

PATENT NO. : 9,950,187 B2
APPLICATION NO. : 15/283105
DATED : April 24, 2018
INVENTOR(S) : Marcelo Soto Thompson Page 1 of 1

It is certified that error appears in the above-identified patent and that said Letters Patent is hereby corrected as shown below:

On the Title Page

Item [73] after "Verberod" delete "Country".

In the Specification

Column 1, Line 9, After "continuation" insert --of--.

Columns 1-2, Line 67 (Column 1) and Line 1 (Column 2), Change "haematoporphyrin" to --hematoporphyrin--.

Column 9, Line 32, After "removed" insert --.--.

Signed and Sealed this
Twenty-eighth Day of May, 2019

Andrei Iancu
*Director of the United States Patent and Trademark Office*